(12) United States Patent
Schmode (10) Patent No.: US 11,229,502 B1
(45) Date of Patent: Jan. 25, 2022

(54) INSTRUMENT CLEANING SYSTEMS AND METHODS

(71) Applicant: Knight LLC, Irvine, CA (US)

(72) Inventor: Sven Schmode, Irvine, CA (US)

(73) Assignee: Knight, LLC, Irvine, CA (US)

( * ) Notice: Subject to any disclaimer, the term of this patent is extended or adjusted under 35 U.S.C. 154(b) by 412 days.

(21) Appl. No.: 15/996,520

(22) Filed: Jun. 3, 2018

Related U.S. Application Data (60) Provisional application No. 62/514,836, filed on Jun. 3, 2017.

(51) Int. Cl.
| | |
|---|---|
| *A61B 90/70* | (2016.01) |
| *A61L 2/24* | (2006.01) |
| *A61L 2/18* | (2006.01) |
| *A61B 1/12* | (2006.01) |
| *C11D 3/48* | (2006.01) |

(52) U.S. Cl.
CPC .............. *A61B 90/70* (2016.02); *A61B 1/122* (2013.01); *A61L 2/18* (2013.01); *A61L 2/24* (2013.01); *A61B 2090/701* (2016.02); *A61L 2202/14* (2013.01); *A61L 2202/17* (2013.01); *A61L 2202/24* (2013.01); *C11D 3/48* (2013.01)

(58) Field of Classification Search
None
See application file for complete search history.

(56) References Cited

U.S. PATENT DOCUMENTS

| | | | |
|---|---|---|---|
| 3,178,756 A | 4/1965 | Ballantyne | |
| 3,181,196 A | 5/1965 | Knightly | |
| 3,563,418 A | 2/1971 | Hahn | |
| 3,709,437 A | 1/1973 | Wright | |
| 3,822,217 A | 7/1974 | Rogers | |
| 3,961,754 A | 6/1976 | Kuhns et al. | |
| 4,743,430 A | 5/1988 | Spielholz | |
| 6,042,089 A | 3/2000 | Klein | |
| 6,082,586 A | 7/2000 | Banks | |
| D448,451 S * | 9/2001 | Turnbull | ...................... D23/226 |
| 6,286,527 B1 * | 9/2001 | Stanley | .................. A01N 37/16 |
| | | | 134/169 C |
| 7,641,132 B2 * | 1/2010 | Richards | .................. A62C 5/02 |
| | | | 239/349 |

(Continued)

FOREIGN PATENT DOCUMENTS

EP    1839680 A1    10/2007

OTHER PUBLICATIONS

Ebiox Advanced Decontamination Technology, www.ebiox.co.uk, Advanced Instrument Cleaning brochure, dated Mar. 2014.

*Primary Examiner* — Rita P Adhlakha
(74) *Attorney, Agent, or Firm* — Stout, Uxa & Buyan, LLP; Donald E. Stout (57) ABSTRACT

An automated medical instrument cleaning system is particularly adapted to provide a complete application of wet/dry detergent foam to medical instruments in a point of use cleaning operation for instrument reprocessing, in a consistent and fully adjustable manner. The system comprises a microprocessor, a user interface, and an adjustable wand for the application of foam that covers surface and internal lumens of the instruments to be cleaned, using wand applicators, to quickly and easily coat all external and internal instrument surfaces with detergent foam before the bio burden has a chance to harden.

13 Claims, 6 Drawing Sheets

(56) References Cited

U.S. PATENT DOCUMENTS

| | | | |
|---|---|---|---|
| 8,057,117 B2 | | 11/2011 | Perlman et al. |
| D660,541 S | * | 5/2012 | Trentadue ................... D34/25 |
| 2011/0031272 A1 | * | 2/2011 | Comiskey ................ G01F 3/10 |
| | | | 222/23 |
| 2011/0315788 A1 | * | 12/2011 | Henderson .......... A01M 7/0046 |
| | | | 239/152 |
| 2013/0056497 A1 | | 3/2013 | McNulty et al. |
| 2014/0231545 A1 | | 8/2014 | Analetto et al. |

* cited by examiner

INSTRUMENT CLEANING SYSTEMS AND METHODS

This application claims the benefit under 35 U.S.C. 119(e) of the filing date of Provisional U.S. Application Ser. No. 62/514,836, entitled Instrument Cleaning Systems and Methods, and filed on Jun. 3, 2017, which application is herein expressly incorporated by reference, in its entirety.

BACKGROUND OF THE INVENTION

Although medical science has made tremendous advances in the past few decades, improving greatly the quality of life and longevity of patients, infectious diseases continue to plague society, and especially these other advances. Such infections, particular in hospital settings, have become very stubborn and difficult to treat, particularly as antibiotic resistance has increased, and thus alternatives for treating infections have diminished.

Unfortunately, current cleaning approaches usually involve a manual application of detergent spray, which does not cover and invade internal lumens, or, sometimes, external surface features, such as channels or other protected areas. This shortcoming allows organic contaminants to remain embedded on or within used medical instruments, potentially causing infection problems when re-used.

Accordingly, it has become more important than ever to ensure that reusable medical instruments are thoroughly cleaned and sanitized between uses, and improved systems for ensuring same are needed.

SUMMARY OF THE INVENTION

The present invention is an automated medical instrument cleaning system particularly adapted to provide a complete application of wet/dry detergent foam to medical instruments in a point of use cleaning operation for instrument reprocessing, in a consistent and fully adjustable manner. The system comprises a microprocessor, a user interface, and an adjustable wand for the application of foam that covers surface and internal lumens of the instruments to be cleaned, using wand applicators, to quickly and easily coat all external and internal instrument surfaces with detergent foam before the bio burden has a chance to harden.

The inventive system manually converts detergent into foam for pre-cleaning and pre-soaking medical instruments.

The resultant system is operator-friendly, with hand pieces or wands for coating all surfaces to be cleaned, with no need for hand spraying. The density of the foam produced from a liquid detergent supply is programmable, according to application. A tray mode is provided for directing a higher flow of foam to coat the exterior surface of an instrument, where indicated. A channel mode is provided for directing a lower flow of foam to coat the interior of an instrument channel or passageway within the instrument.

Applications for the inventive system include hospitals, surgical operating rooms, surgery centers, and sub-sterile areas for applying pre-treatment detergent foam. The microprocessor control and interface allows the user to adjust delivery to consistently cover instruments of any configuration or quantity.

More particularly, there is provided a system for cleaning medical instruments, which comprises a housing having an interior volume and a door which may be open or closed for controlling access to the interior volume. A panel is disposed on the door. A user interface, comprising user-activated keys and a display screen, is disposed on the panel. A controller s disposed within the housing and operatively connected to the user interface. A chemical inflow line is adapted to receive chemicals into the system from a chemical reservoir. A pump is disposed in the housing which is adapted to pump chemicals through the chemical inflow line from the chemical reservoir. An air compressor is disposed in the housing, and an air tank is disposed in the housing and operatively connected to the air compressor for storing a supply of compressed air. A chemical outlet line extends from the pump, a compressed air outlet line extends from the air tank, and a wand is provided for dispensing generated detergent foam. The wand comprises an outlet nozzle, a mixing chamber, a chemical inlet line fluidly connected to the chemical outlet line, and a compressed air inlet line fluidly connected to the compressed air outlet line. The outlet nozzle is fluidly connected to the mixing chamber. The controller, a microcontroller in exemplary embodiments, adjusts flow rates of the chemical and the compressed air into the mixing chamber to create a generated detergent foam having desired characteristics for specified applications.

In exemplary embodiments, the chemical inflow line is attached to a chemical suction tube which is adapted for receiving an inflow of chemical from a reservoir. The wand comprises a tray cleaning wand. The tray cleaning wand has a tip applicator comprising a plurality of outlets for delivering a plurality of streams of generated detergent foam to a cleaning tray. The wand may also comprise a channel cleaning wand. The channel cleaning wand has a tip applicator comprising a single outlet for delivering a fine stream of generated detergent foam to one or more channels of a medical instrument. Either wand may hang from a side panel of the housing when not in use.

The system may further comprise a second wand for dispensing a generated detergent foam, the second wand comprising an outlet nozzle, a mixing chamber, a chemical inlet line fluidly connected to the chemical outlet line, and a compressed air inlet line fluidly connected to the compressed air outlet line, the outlet nozzle being fluidly connected to the mixing chamber. The wand and the second wand have different tip applicators for dispensing streams of generated detergent foam in different patterns and flow rates suited to different cleaning applications.

The controller includes a memory in which are stored a plurality of settings for creating generated detergent foam, each setting including delivery of a predetermined amount of compressed air and a predetermined amount of the chemical to the wand mixing chamber for creating a generated detergent foam having predetermined characteristics suitable for a predetermined cleaning application. The controller ensures delivery of the predetermined amount of compressed air by operating a valve to release the predetermined amount of compressed air from the air tank and further ensures delivery of the predetermined amount of the chemical by operating the pump at an appropriate speed.

The wand comprises a trigger disposed thereon for actuating the system to deliver generated detergent foam.

In another aspect of the invention, there is described a method of creating and applying generated detergent foam for a particular cleaning application. The method comprises steps of actuating a start button on a user interface panel to initiate a foam generating cycle, actuating a valve to release a predetermined amount of compressed air from an air tank disposed in a housing outside of the housing and into a mixing chamber disposed in a dispensing wand, and actuating a chemical pump to draw a predetermined supply of a cleaning chemical from a reservoir through the pump and then into the mixing chamber. Further steps include mixing the compressed air and the cleaning chemical to create a generated detergent foam having predetermined characteristics and dispensing the generated detergent foam from an applicator tip disposed on the wand into an object to be cleaned or a tray to store cleaning solution. A controller is used to perform the steps of actuating the valve, and actuating the chemical pump automatically. The controller is programmed to store a plurality of different foam generating settings, and the step of actuating a start button includes a step of selecting a particular foam generating setting. The controller adjusts the quantities of chemical pumped and compressed air released into the mixing chamber according to the selected particular foam generating setting.

The invention, together with additional features and advantages thereof, may be best understood by reference to the following description taken in conjunction with the accompanying illustrative drawings. In these accompanying drawings, like reference numerals designate like parts throughout the figures.

DESCRIPTION OF THE PREFERRED EMBODIMENT

Figure 1:
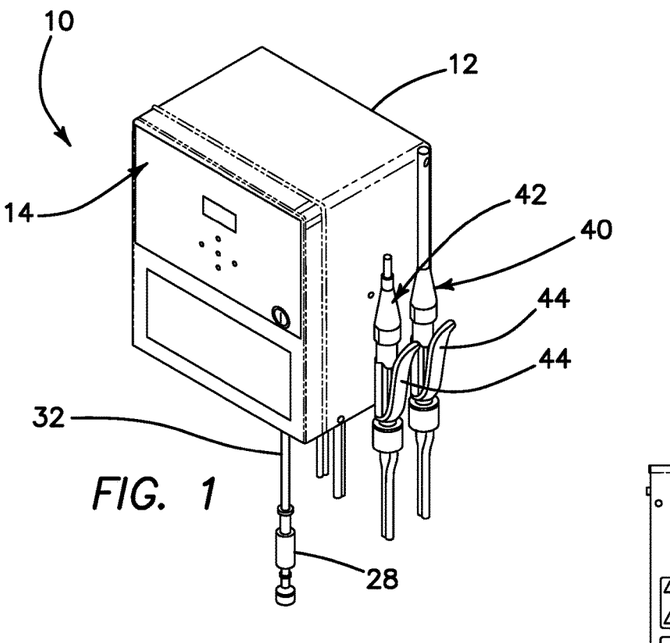
FIG. 1 is an isometric view of a system constructed in accordance with one exemplary embodiment of the present invention.
Figure 2:
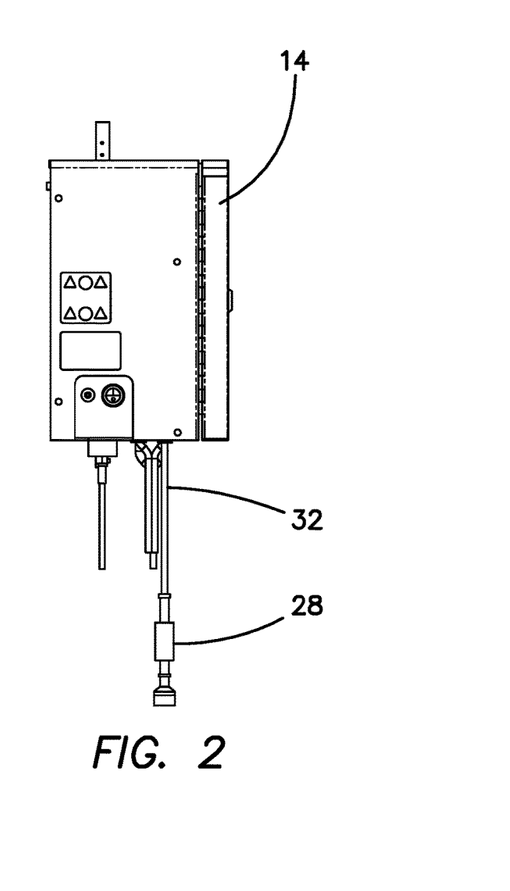
FIG. 2 is a view of a the left side of the system shown in FIG. 1.
Figure 3:
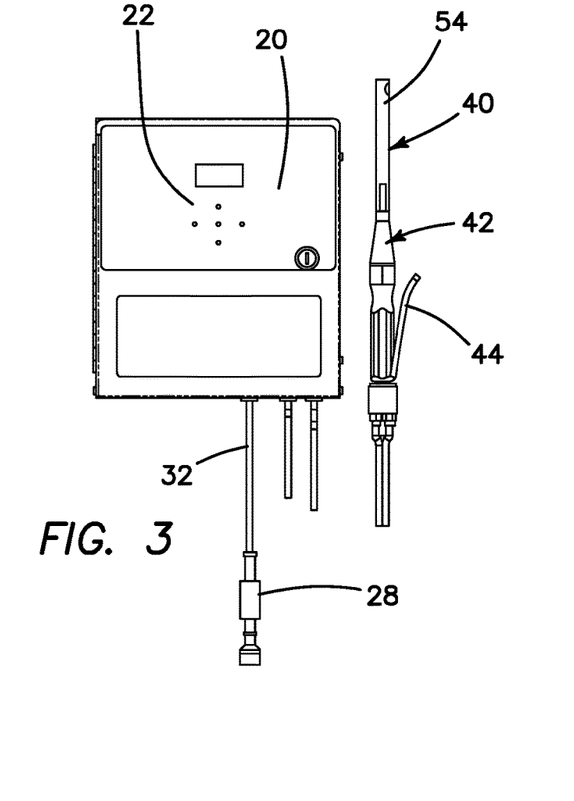
FIG. 3 is frontal view of the system shown in FIGS. 1 and 2.
Figure 4:
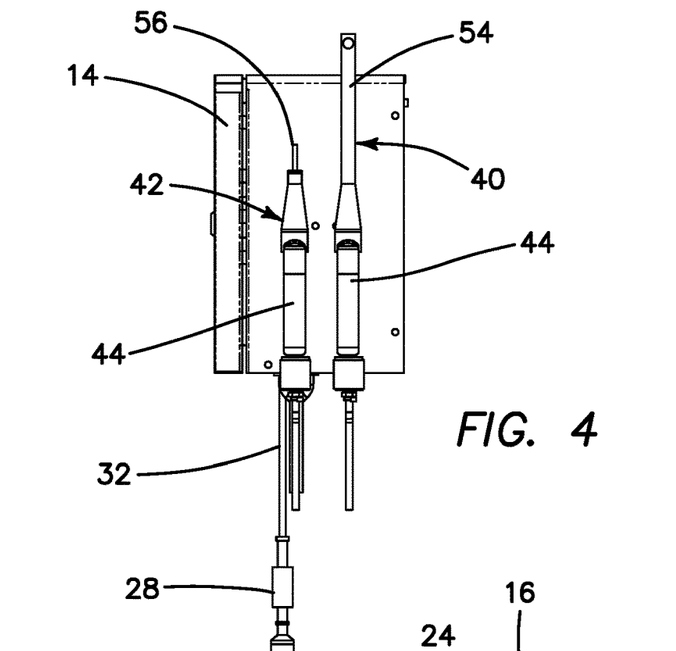
FIG. 4 is a view of the right side of the system shown in FIGS. 1-3.
Figure 5:
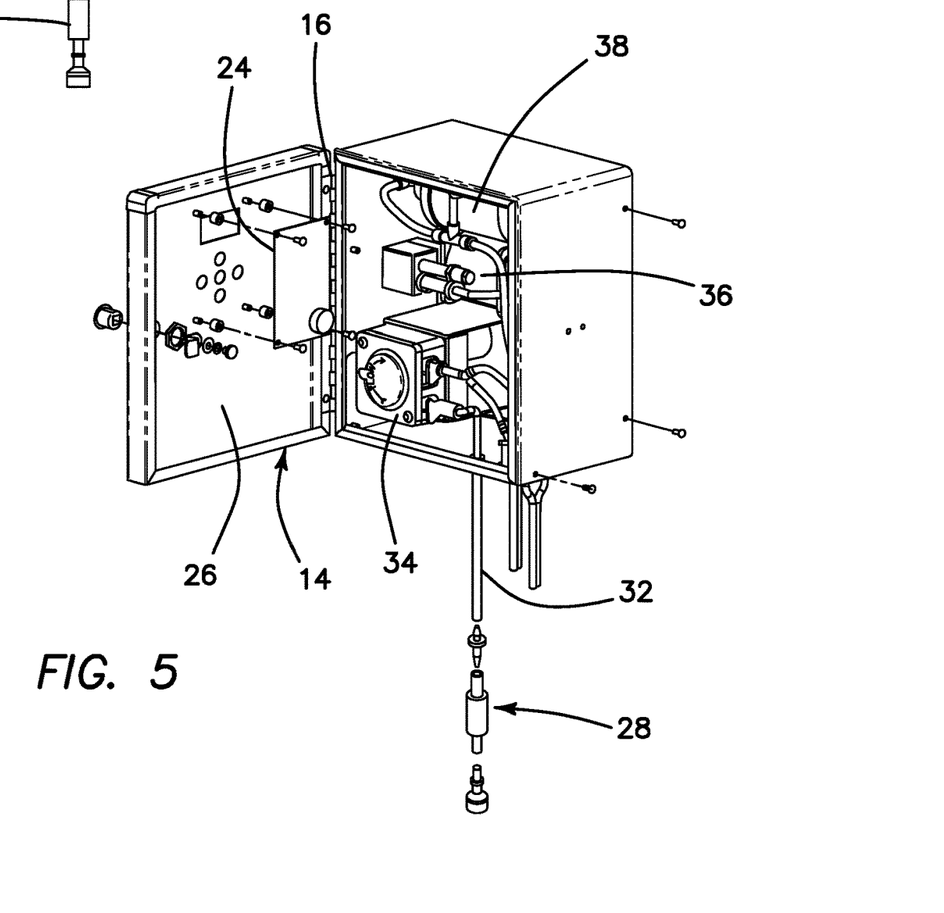
FIG. 5 is an isometric view of the control box of the system shown in FIG. 1, wherein an access door is open to illustrate the interior system components.

Referring now more particularly to the drawings, there is shown in FIGS. 1-6 a foam generating and dispensing system 10 comprising a housing 12, typically formed of a suitable metal or plastic, which includes a door 14 movable about a hinge 16 (FIG. 5) between an open orientation, as shown in FIG. 5, and a closed orientation, as shown in FIGS. 1-4 and 6. The housing 12 may be mounted to a wall or other suitable location at a point of use, or may be portably mounted to an IV stand 18 or the like, as shown, for example, in FIG. 10.

A front panel 20 of the door 14 includes a user interface 22 which includes programming keys, a start key, a display and the like to operate the system. An advanced microcontroller 24 is disposed behind the user interface 22, on the inside panel 26 of the door 14 (FIG. 5) for system operation and control, including power settings, foam generation processes, pump speeds, air compressor operation, air tank fill/refill cycles, and pump on/off intervals.

Figure 10:
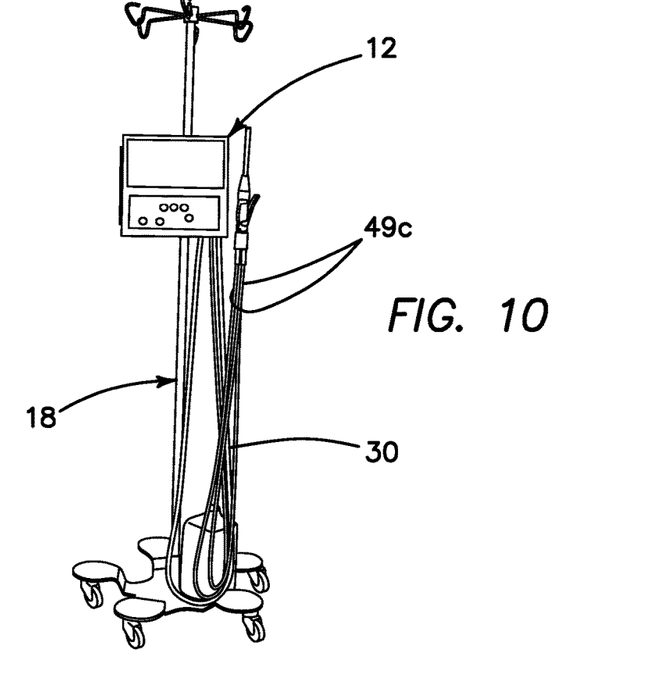
FIG. 10 is an isometric view illustrating an exemplary embodiment of the system of the present invention mounted on an easily transportable pole assembly.
Figure 11:
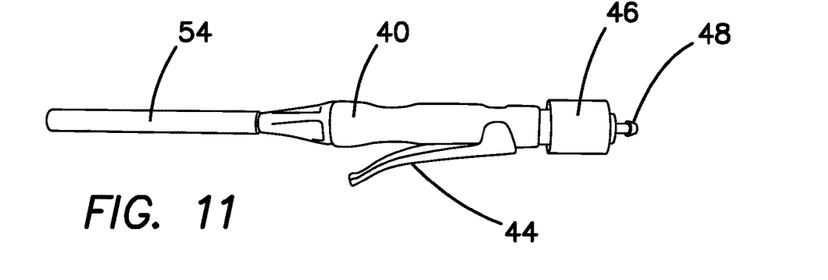
FIG. 11 is an illustration of an exemplary wand for dispensing generated foam to pre-clean instruments disposed in a tray.
Figure 12:
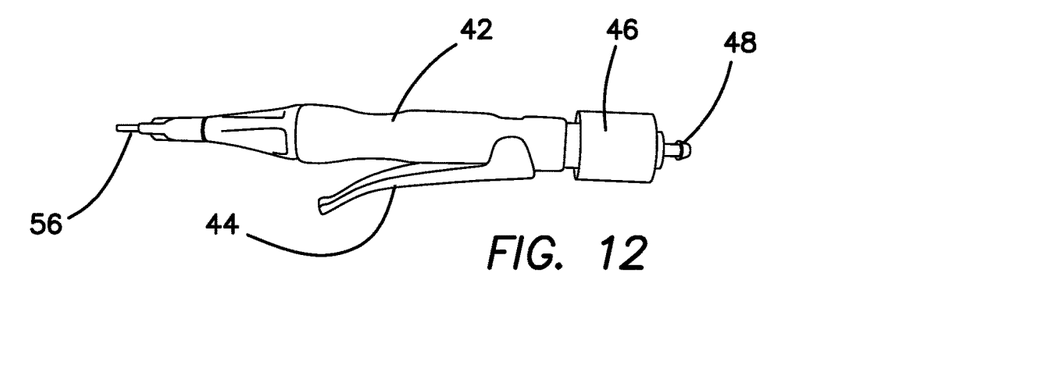
FIG. 12 is an illustration of an exemplary wand for dispensing generated foam to pre-clean interior channels of medical instruments.

Remaining elements of the system include a chemical suction tube 28 which is adapted for receiving an inflow of chemical (typically detergent) from a reservoir 30 (such as the one gallon bottle shown, for example, in FIG. 10). Inflowing detergent enters the housing 12 through inflow line 32 and is pumped by a chemical motor/pump 34. An air compressor 36, an air tank 38, and an air solenoid valve 39 are also provided, and disposed within the housing 12. The purpose of these components is to supply, on demand, suitable supplies of detergent and compressed air for mixing to create the foam which is dispensed onto or into the instruments to be cleaned.

The foam cleaning solution generated by the system 10 is dispensed by one or more wands supplied with the system. As illustrated, a tray wand 40 and a channel wand 42 are provided with the system 10, and are stored by hanging them on the side of the housing 12, as shown in FIGS. 1, 4, 6, and 10, for example. Of course, only one or the other of the wands 40 and 42 may be provided, if desired, and additional wands may be designed and used for specific cleaning applications.

In operation, the user interface 22 is utilized to program a desired foam density for a particular cleaning application. For example, in tray cleaning mode, using the tray wand 40, a higher flow of foam is desirable for coating the exterior of the instrument. In one particular example, the foam concentrate dosing speed is 60% for tray cleaning applications (60% chemical to 40% air), and 5% for channel cleaning applications (5% chemical to 95% air). Minimum and maximum air pressure is also programmed. Higher minimum/maximum air pressure settings produce a dryer foam with smaller bubble diameters and thinner membranes. Too much air pressure may cause sputtering of the foam stream coming out of the wand orifices. Not enough air pressure may leave foams too wet and cause excess usage. A careful balance of the right pump concentrate speed along with the right air mixture will produce the foam durability and quality that is right for the application. These foaming programs may be pre-set in the system, once calibrated, to ensure repeated success with each cleaning operation.

Figure 6:
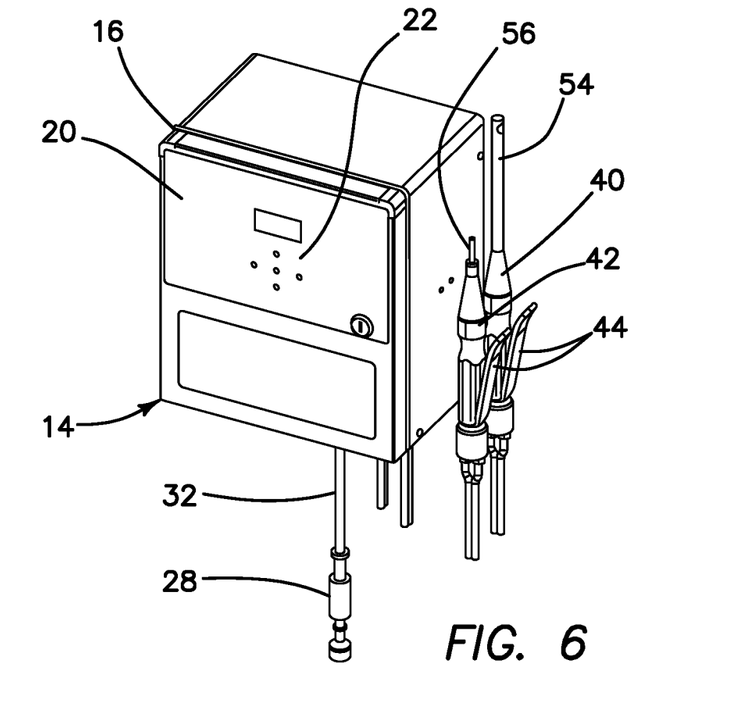
FIG. 6 is an isometric view of the system and control box shown in FIGS. 1-5, wherein the access door is closed.
Figure 7:
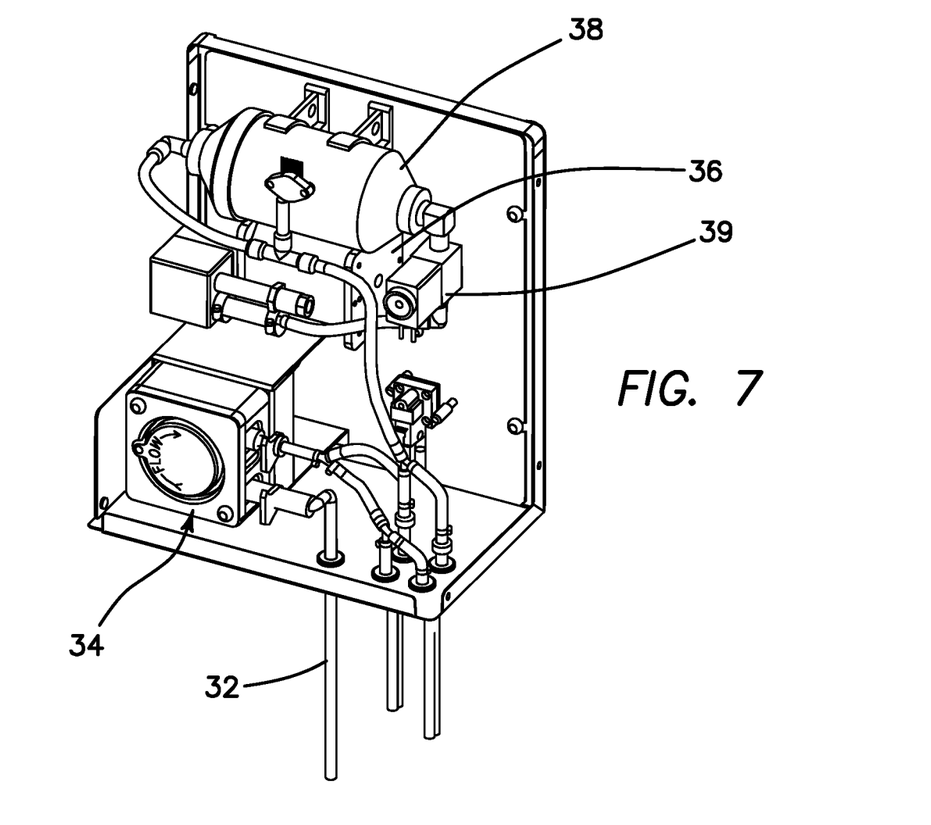
FIG. 7 is an isometric view of the interior system components of an exemplary embodiment of the present invention.
Figure 8:
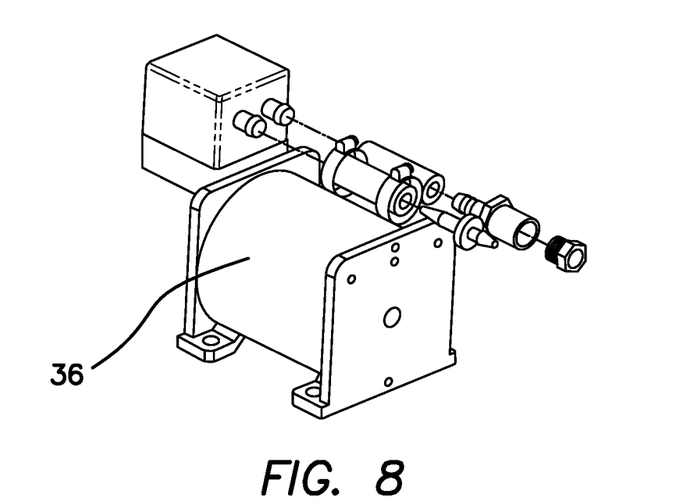
FIG. 8 is an isometric view, in isolation, of an exemplary embodiment of the air compressor assembly of the present invention.
Figure 9:
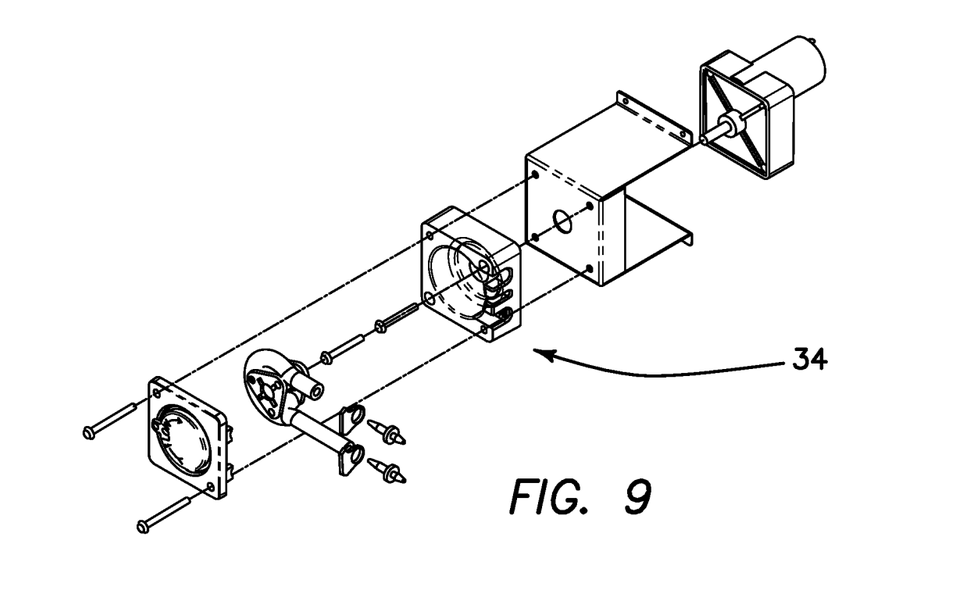
FIG. 9 is an exploded isometric view of an exemplary embodiment of the chemical motor assembly of the present invention.

At the press of a trigger 44 on either of the foaming wands 40, 42, the chemical pump 34 pumps the detergent at the pre-programmed rate to a mixing chamber 46 through a dual inlet 48. Simultaneously, compressed air is delivered from the air tank 38 into the mixing chamber 46 at the pre-programmed rate, also through the dual inlet 48, wherein the detergent is foamed to the programmed extent. The inlet 48 for each wand 40, 42 comprises a chemical inlet 48*a* and a compressed air inlet 48*b*, as shown in FIG. 6. A dual channel outlet 49*a* extends from the housing 12 to deliver both chemical from the pump 34 and compressed air from the tank 38 to the dual inlet 48 of the wand 40. A second dual channel outlet 49b extends from the housing 12 to deliver both chemical from the pump 34 and compressed air from the tank 38 to the dual inlet 48 of the wand 42. The dashed lines extending from each dual channel outlet 49a, 49b to its respective dual inlet 48 represents a hose fluidly connecting the outlets to their respective inlets, which may be of any desired length according to design applications, which hoses 49c are illustrated in FIG. 10.

The dual channels in the respective housing outlets 49a, 49b and wand inlets 48 are constructed to permit dual and separate flow of chemical from pump 34 and compressed air from air tank 38 out of the housing and into the mixing chamber 46 of the wand 40, 42, without premixing.

Figure 13:
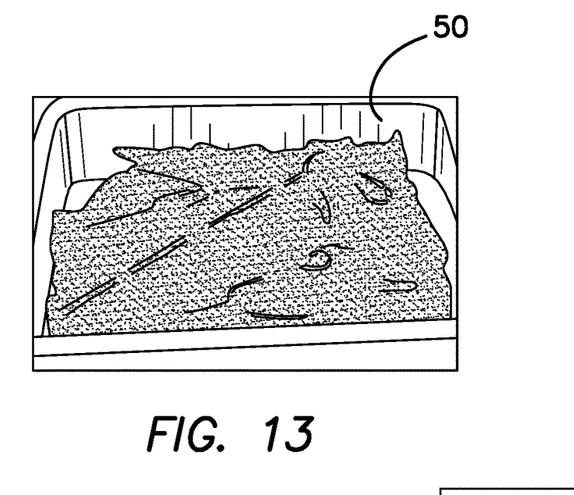
FIG. 13 is an illustration of a typical tray for pre-cleaning instruments with an appropriate amount of foam disposed therein.
Figure 14:
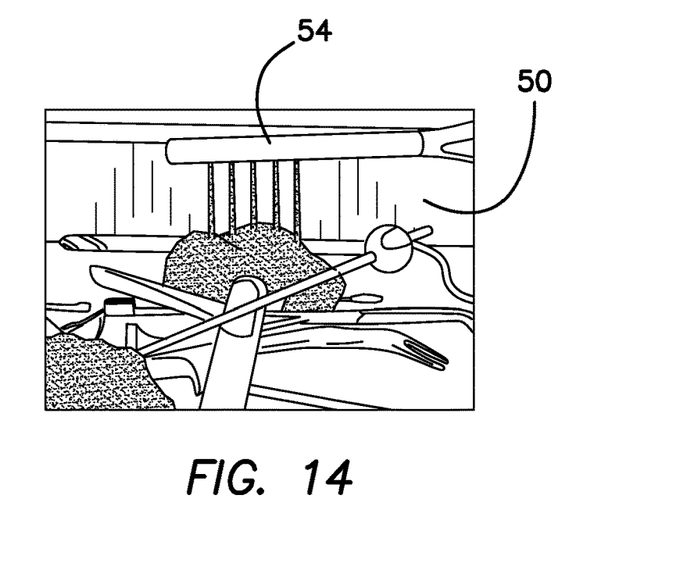
FIG. 14 is an illustration showing foam being dispensed in a plurality of streams from the tray wand of FIG. 11.
Figure 15:
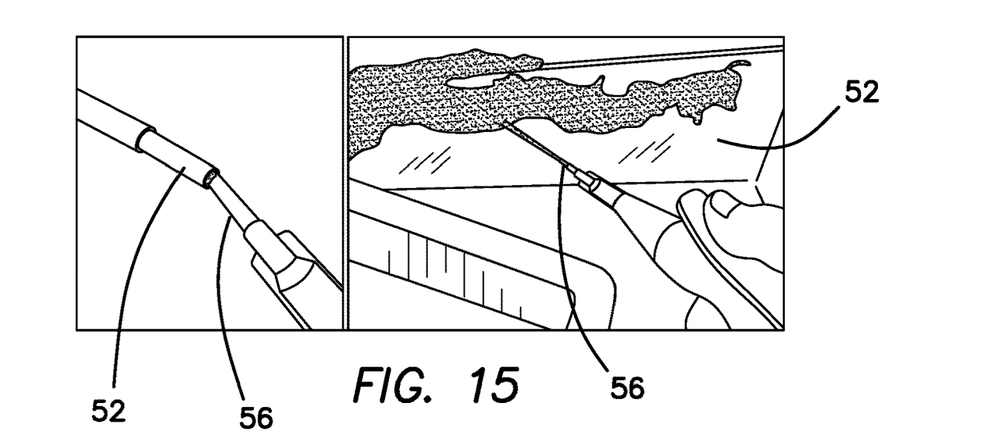
FIG. 15 is an illustration foam being dispensed from the channel wand of FIG. 12.

More particularly, the detergent foam meets with the desired air flow in the mixing chamber 46, wherein the detergent and air mix and agitate to the desired foam texture and exit the wand through one or the other tip applicator. The generated detergent foam is then delivered to the desired site, whether that be a tray 50 (FIG. 13) or the interior channels of an instrument 52 (FIG. 15). As shown in FIG. 14, a first tip applicator 54 of the tray wand 40 may be adapted to deliver foam to the tray 50 in several streams. FIG. 13 illustrates an appropriate amount of foam covering the instruments disposed in the tray 50. In FIG. 15, a second tip applicator 56 is utilized to deliver a fine stream of penetrating foam into a wide range of cannulated instruments, such as laparoscopes, semi-rigid endoscopes, drill bits, suctions, and flexible endoscope channels.

Foam provides a great visual marker for where the detergent has been applied on the instrument surfaces.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A system for cleaning medical instruments, comprising:
   a housing having an interior volume and a door which may be open or closed for controlling access to the interior volume;
   a panel disposed on the door;
   a user interface, comprising user-activated keys and a display screen, disposed on the panel;
   a controller disposed within the housing and operatively connected to the user interface;
   a chemical inflow line adapted to receive chemicals into the system from a chemical reservoir;
   a pump disposed in the housing which is adapted to pump chemicals through the chemical inflow line from the chemical reservoir;
   an air compressor disposed in the housing:
   an air tank disposed in the housing and operatively connected to the air compressor for storing a supply of compressed air;
   a chemical outlet line extending from the pump;
   a compressed air outlet line extending from the air tank; and
   a wand adapted to dispense generated detergent foam, the wand comprising an outlet nozzle, a mixing chamber, a chemical inlet line fluidly connected to the chemical outlet line, and a compressed air inlet line fluidly connected to the compressed air outlet line, the outlet nozzle being fluidly connected to the mixing chamber;
   wherein the controller adjusts flow rates of the chemical and the compressed air flowing into the mixing chamber to create a generated detergent foam having desired characteristics for specified applications.

2. The system as recited in claim 1, wherein the controller comprises a microcontroller.

3. The system as recited in claim 1, wherein the chemical inflow line is attached to a chemical suction tube which is adapted for receiving an inflow of chemical from a reservoir.

4. The system as recited in claim 1, wherein the wand comprises a tray cleaning wand.

5. The system as recited in claim 4, wherein the tray cleaning wand has a tip applicator comprising a plurality of outlets for delivering a plurality of streams of generated detergent foam to a cleaning tray.

6. The system as recited in claim 1, wherein the wand comprises a channel cleaning wand.

7. The system as recited in claim 6, wherein the channel cleaning wand has a tip applicator comprising a single outlet for delivering a fine stream of generated detergent foam to one or more channels of a medical instrument.

8. The system as recited in claim 1, wherein the wand is adapted to hang from a side panel of the housing when not in use.

9. The system as recited in claim 1, and further comprising a second wand adapted to dispense a generated detergent foam, the second wand comprising an outlet nozzle, a mixing chamber, a chemical inlet line fluidly connected to the chemical outlet line, and a compressed air inlet line fluidly connected to the compressed air outlet line, the outlet nozzle being fluidly connected to the mixing chamber.

10. The system as recited in claim 9, wherein the wand and the second wand have different tip applicators for dispensing streams of generated detergent foam in different patterns and flow rates suited to different cleaning applications.

11. The system as recited in claim 1, wherein the controller includes a memory in which are stored a plurality of settings for creating generated detergent foam, each setting including delivery of a predetermined amount of compressed air and a predetermined amount of the chemical to the wand mixing chamber for creating a generated detergent foam having predetermined characteristics suitable for a predetermined cleaning application.

12. The system as recited in claim 11, wherein the controller ensures delivery of the predetermined amount of compressed air by operating a valve to release the predetermined amount of compressed air from the air tank and further ensures delivery of the predetermined amount of the chemical by operating the pump at an appropriate speed.

13. The system as recited in claim 1, wherein the wand comprises a trigger disposed thereon for actuating the system to deliver generated detergent foam.

* * * * *